United States Patent [19]

Lindemann et al.

[11] Patent Number: 4,550,193

[45] Date of Patent: Oct. 29, 1985

[54] PROCESS FOR THE PREPARATION OF 2,3-DIMERCAPTOSUCCINIC ACID AND ITS LOWER ALKYL ESTERS

[75] Inventors: Martin K. O. Lindemann, Bridgewater; Elvin R. Lukenbach, Somerset, both of N.J.

[73] Assignee: Johnson & Johnson Baby Products Company, New Brunswick, N.J.

[21] Appl. No.: 385,953

[22] Filed: Jun. 7, 1982

[51] Int. Cl.$^4$ ............... C07C 149/20; C07C 148/00
[52] U.S. Cl. .............. 560/147; 260/453 RY; 562/594
[58] Field of Search .......... 560/147; 562/594; 260/453 RY

[56] References Cited

U.S. PATENT DOCUMENTS 2,594,030  4/1952  Coons et al. ............ 562/594
3,616,373  10/1971  Heiba ..................... 562/594
4,172,207  10/1979  Mack ...................... 562/594

FOREIGN PATENT DOCUMENTS 395967  1/1966  Switzerland ............ 562/594

Primary Examiner—Vivian Garner
Attorney, Agent, or Firm—Steven P. Berman

[57] ABSTRACT 2,3-dimercaptosuccinic acid and esters thereof are prepared by reacting sodium thiosulfate with acetylene dicarboxylic acid in the presence of a strong acid and subjecting the resulting alkylthiosulfate to an acid hydrolysis. The 2,3-dimercaptosuccinic acids and esters thereof are useful as an antidote for heavy metal poisoning.

5 Claims, No Drawings

PROCESS FOR THE PREPARATION OF 2,3-DIMERCAPTOSUCCINIC ACID AND ITS LOWER ALKYL ESTERS

BACKGROUND OF THE INVENTION

The present invention relates to a process for the preparation of 2,3-dimercaptosuccinic acid and esters thereof. The 2,3-dimercaptosuccinic acids and esters thereof which can be prepared by the present process may be represented by the formula:

$$\begin{array}{c} COOR \\ | \\ H-C-SH \\ | \\ H-C-SH \\ | \\ COOR \end{array}$$

wherein R is H or lower alkyl containing from 1 to 3 carbon atoms. When R is H, then the 2,3-dimercaptosuccinic acid is prepared and when R is lower alkyl, the corresponding esters are prepared.

The prior art teaches a two-step synthesis of 2,3-dimercaptosuccinic acid involving the addition of two moles of thiolacetic acid across the triple bond of acetylene dicarboxylic acid followed by an alkaline hydrolysis of the resulting 2,3-diacetyldimercaptosuccinic acid. This can be shown schematically as follows:

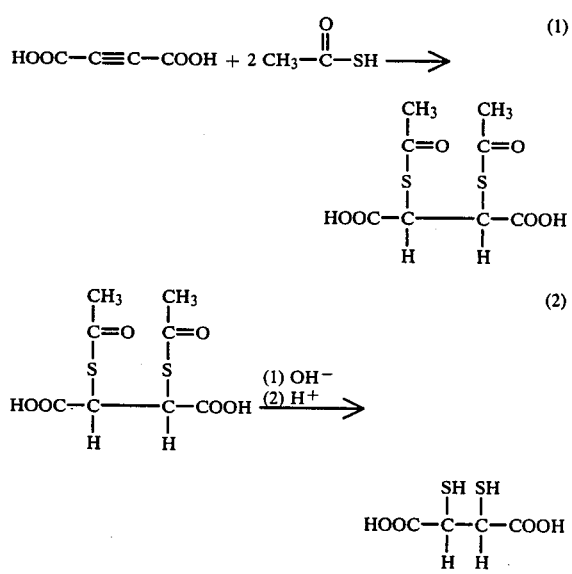

Although this process results in the preparation of the desired compound, it requires the use of thiolacetic acid which is toxic and also expensive.

It is, therefore, an object of this invention to provide a novel process for the preparation of 2,3-dimercaptosuccinic acid and esters thereof.

It is a further object of this invention to provide a process for the preparation of 2,3-dimercaptosuccinic acid and esters thereof which does not require the use of thiolacetic acid.

Other objects and advantages of the present invention will be apparent from the following description.

SUMMARY OF THE INVENTION

The foregoing objects are achieved in a two-step synthesis of 2,3-dimercaptosuccinic acid wherein the first step requires the addition of 2 moles of sodium thiosulfate to acetylene dicarboxylic acid in the presence of a strong acid to yield an alkylthiosulfate. A strong acid, i.e., pH below about 4 is desired otherwise the reaction is hindered. Acids such as trichloroacetic acid, trifluoroacetic acid, methanesulfonic acid, formic acid, acetic acid, sulfuric acid and hydrochloric acid, for example, may be employed. This reaction should be carried out at temperatures below room temperature to prevent decomposition of the sodium thiosulfate and premature hydrolysis of the resulting alkylthiosulfate.

The resulting alkylthiosulfate is then subjected to an acid hydrolysis in the presence of a suitable solvent to yield the desired 2,3-dimercaptosuccinic acid. Strong acids such as trichloroacetic acid, trifluoroacetic acid, methanesulfonic acid, conc. sulfuric acid and conc. hydrochloric acid are suitable. Suitable solvents are those with a sufficient solubility for the reactants and include water, water-methanol, water-dioxane and the like. The reaction can be carried out at temperatures up to about 80° C.

The reactions are normally carried out at atmospheric pressure; however, should a reaction appear to be sluggish, higher pressures can be used in order to raise the temperature and allow the reaction to proceed.

The general reactions of the present invention can be illustrated schematically as follows:

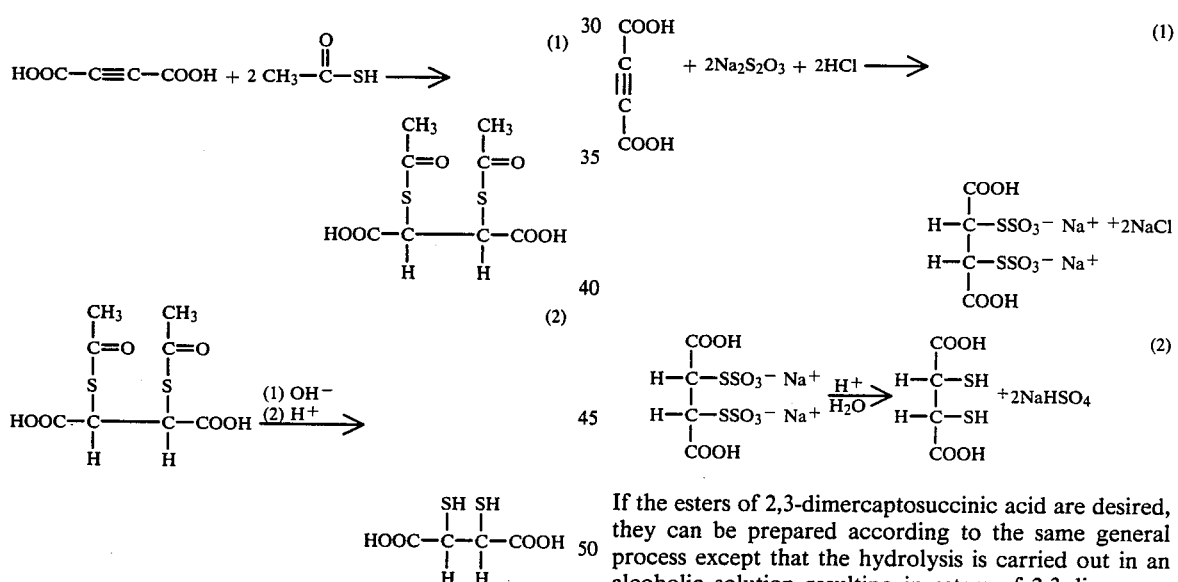

If the esters of 2,3-dimercaptosuccinic acid are desired, they can be prepared according to the same general process except that the hydrolysis is carried out in an alcoholic solution resulting in esters of 2,3-dimercaptosuccinic acid of the formula $$\begin{array}{c} COOR \\ | \\ H-C-SH \\ | \\ H-C-SH \\ | \\ COOR \end{array}$$

wherein R is lower alkyl of from 1 to 3 carbon atoms.

The resulting 2,3-dimercaptosuccinic acids and esters have been demonstrated to be useful as an antidote for heavy metal poisoning, especially lead poisoning, in humans. Its effectiveness for this utility is based on its ability to form a soluble complex with any lead or other heavy metal present in the system which is then readily excreted. This property is more fully discussed in the literature, see, for example, J. H. Graziano et al., J. Pharmaco Pharmacol. Exp. Ther. 206,696–700(1978) and L. L. Egorova, Zh. Obsch. Khim, 42, 2240(1972).

The following examples will illustrate in detail the manner in which the present invention may be practised. It will be understood, however, that the invention is not confined to the specific limitations set forth in the individual examples, but rather to the scope of the appended claims.

EXAMPLE I 11.4 g (0.1 moles) of acetylene dicarboxylic acid are dissolved in 400 ml of distilled water. The solution is then transferred into a glass reactor equipped with external cooling, magnetic stirring and pH-stat assembly. After the solution is cooled to 5° C. and the pH adjusted to 3 via the addition of sodium hydroxide, 31.6 g (0.2 moles) of sodium thiosulfate are added. As the reaction produces one hydroxyl ion for each thiosulfate moiety added across the triple bond and the reaction is strongly inhibited by pH values above 5, the reaction mixture is maintained at pH 3 by the addition of 1N HCl via the pH-stat assembly. The reaction is considered complete when the free thiosulfate concentration as estimated by iodometric titration approaches zero and the amount of HCl used is equimolar to the quantity of $Na_2S_2O_3$ employed. After adjusting the pH to 7, the reaction product, tetrasodium 2,3-bisthiosulfatosuccinate, is isolated by removing the water via freeze-drying.

EXAMPLE II

Using a 4 liter glass reactor equipped similarly to the reactor in Example I, 79.9 g (0.7 moles) of acetylene dicarboxylic acid are reacted with 347.2 g (1.4 moles) of sodium thiosulfate pentahydrate. The temperature is kept slightly lower than 5° C. and the pH maintained at 1.5 by the addition of 6N HCl. After 20 hours the consumption of the expected amount of HCl and a negligible thiosulfate titer indicates completion of the reaction. After adjusting the pH to 7 with sodium hydroxide, the reaction mixture is freeze-dried to yield a white powder, which is tetrasodium 2,3-bisthiosulfatosuccinate.

EXAMPLE III

Using the glass reactor of Example II, 114 g (1.0 mole) of acetylene dicarboxylic acid are dissolved in 3 l. of distilled water and 25.9 g of calcium hydroxide are added to raise the pH to 1.3. After chilling the reaction mixture to 5° C., 496.0 g (2.0 moles) of sodium thiosulfate pentahydrate in 500 ml water are added. The pH is maintained at 1.5 by adding 6N $H_2SO_4$ via the pH-stat assembly. When the calculated quantity of sulfuric acid is consumed and the iodometric titer for thiosulfate is negligible the reaction is terminated. The pH is raised to 7 with calcium hydroxide and the resulting calcium sulfate separated by filtration. After freeze-drying, the product, tetrasodium 2,3-bisthiosulfatosuccinate, is obtained as a white powder.

EXAMPLE IV 86 g of the reaction product of Example III are dissolved in a solution of 64 of conc. $H_2SO_4$ in 320 ml of dioxane. The solution is stirred at 55° C. for 1 hour. After cooling, the dioxane solution is separated from a precipitate of inorganic salts. The precipitate is washed with dioxane and the combined dioxane solution concentrated in vacuo to 51.5 g of a white paste; the infrared spectrum of the paste is super-imposable with authentic dimercaptosuccinic acid. Fractionation of the dioxane residue produces crystalline meso-dimercaptosuccinic acid identical to authentic samples by melting point and infrared spectrum.

EXAMPLE V 55.6 g of the product of Example I in a mixture of 200 ml methanol and 50 ml 6N HCl are warmed at 70° C. for 2 hours. On cooling, solids separate from the reaction mixture which is removed by filtration and the filtrate is concentrated in vacuo to provide the product as a light-yellow paste, from which crystalline meso-dimercaptosuccinic acid is obtained by crystallization from methanol.

EXAMPLE VI 12 g of the product of Example III in 100 ml of 20% HCl containing 3 ml of ethylene glycol are heated at 90° for 7 hours. On cooling, salts precipitate which are removed and the filtrate on evaporation yields the product as a yellow gum. Crystallization from methanol/acetone provides crystalline meso-dimercaptosuccinic acid.

EXAMPLE VII 5 g of the salt of Example III in a mixture of 100 ml of methanol and 10 ml conc. $H_2SO_4$ are heated at a boil for 24 hours. The reaction mixture is concentrated in vacuo and partitioned between water and ethyl acetate. Evaporation of the ethyl acetate layer yields 2.24 g of the dimethyl ester of dimercaptosuccinic acid identified by infrared spectroscopy and chromatography against authentic samples. Further purification is effected by extraction of the crude product in ether into 1N NaOH, followed by acidification to pH 4 and extraction into ethyl acetate.

EXAMPLE VIII 5.5 g of the salt of Example I are dissolved in a solution of 20 ml conc. HCl in 100 ml abs. ethanol. The solution is boiled for 24 hours, concentrated, and partitioned between ether and water. The ether solution is extracted with aqueous bicarbonate. The aqueous layer is acidified to pH 3 and extracted with ether and concentration of the ether layer yields the diethyl ester of dimercaptosuccinic acid.

What is claimed is:

1. The process for the preparation of 2,3-dimercaptosuccinic acid and esters thereof of the formula

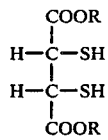

wherein R is H or lower alkyl of from 1 to 3 carbon atoms comprising the steps of
   (1) reacting at a temperature below room temperature sodium thiosulfate with acetylene dicarboxylic acid in the presence of a strong acid with a pH below about 4 to from an alkylthiosulfate; and
   (2) subjecting said alkylthiosulfate to an acid hydrolysis utilizing a strong acid and at a temperature up to about 80° C. said hydrolysis being in the presence of an alcoholic solution when said esters are prepared.
2. The process of claim 1 wherein R is H.
3. The process of claim 1 wherein R is lower alkyl of from 1 to 3 carbon atoms.
4. The process of claim 1 wherein R is methyl.
5. The process of claim 1 wherein R is ethyl.

UNITED STATES PATENT AND TRADEMARK OFFICE
CERTIFICATE OF CORRECTION

PATENT NO. : 4,550,193
DATED      : October 29, 1985
INVENTOR(S) : Lindemann et al.

It is certified that error appears in the above—identified patent and that said Letters Patent are hereby corrected as shown below:

Column 4, line 58 -- "from" -- should read -- "form" --.

Signed and Sealed this

Fourteenth Day of January 1986

[SEAL]

Attest:

Attesting Officer

DONALD J. QUIGG

Commissioner of Patents and Trademarks